United States Patent
Miraki et al.

(10) Patent No.: US 6,248,092 B1
(45) Date of Patent: *Jun. 19, 2001

(54) CATHETERS HAVING A REUSABLE PROXIMAL BODY

(75) Inventors: Manouchehr Miraki, Aliso Viejo; James Passafaro, Santa Ana; Blair Walker, Long Beach; Tom Allen, Laguna Hills; Robert Pecor, Irvine; Jaroslav Janacek, Winchester; Carmen Diaz, Stanton; Laksen Sirimanne, Tustin, all of CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/846,792

(22) Filed: Apr. 30, 1997

Related U.S. Application Data (63) Continuation of application No. 08/265,602, filed on Jun. 24, 1994, now abandoned.

(51) Int. Cl.[7] ................................................. A61M 29/00
(52) U.S. Cl. ..................... 604/96.01; 604/905; 606/195
(58) Field of Search ............................ 604/96, 161, 165, 604/167, 283, 905, 97–104, 533

(56) References Cited

U.S. PATENT DOCUMENTS

| | | | |
|---|---|---|---|
| 3,411,506 | * | 11/1968 | Velasco ................................ 604/101 |
| 3,799,170 | | 3/1974 | Walsh . |
| 3,805,794 | | 4/1974 | Schlesinger . |
| 3,828,782 | * | 8/1974 | Polin ..................................... 604/96 |
| 3,834,394 | | 9/1974 | Hunter et al. . |
| 4,004,588 | * | 1/1977 | Alexander ............................. 604/96 |
| 4,266,550 | * | 5/1981 | Bruner ................................. 604/101 |
| 4,315,513 | * | 2/1982 | Nawash et al. ...................... 604/283 |
| 4,431,426 | * | 2/1984 | Groshong et al. ................... 604/283 |
| 4,600,402 | | 7/1986 | Rosenberg . |
| 4,753,238 | * | 6/1988 | Gaiser ................................. 604/101 |
| 4,771,777 | * | 9/1988 | Horzewski et al. ................. 604/101 |
| 4,772,270 | * | 9/1988 | Wiitta et al. ........................ 604/283 |
| 4,808,165 | * | 2/1989 | Carr ..................................... 606/194 |
| 4,819,637 | | 4/1989 | Dormandy, Jr. et al. . |
| 4,850,969 | | 7/1989 | Jackson . |
| 4,969,879 | * | 11/1990 | Lichte ................................. 604/283 |
| 4,994,033 | * | 2/1991 | Shockey et al. .................... 604/101 |
| 5,154,725 | * | 10/1992 | Leopold ................................ 604/96 |
| 5,156,594 | | 10/1992 | Keith . |
| 5,226,889 | * | 7/1993 | Sheiban .............................. 604/101 |
| 5,261,887 | * | 11/1993 | Walker ................................ 604/161 |
| 5,279,546 | * | 1/1994 | Mische et al. ...................... 604/101 |
| 5,279,562 | * | 1/1994 | Sirhan et al. .......................... 604/96 |

(List continued on next page.)

OTHER PUBLICATIONS

Product Brochure from Arrow International. Oct., 1989.*

*Primary Examiner*—Sharon Kennedy
*Assistant Examiner*—Michael M Thompson
(74) *Attorney, Agent, or Firm*—Heller Ehrman White & McAuliffe LLP (57) ABSTRACT

Catheters including a rugged, reusable proximal body and a disposable distal body attached by a releasable connection are provided. The reusable proximal body is constructed from resterilizable materials such as glass, metal alloys and engineering plastics. The disposable distal body, designed for one-time use, is made from reliable but inexpensive materials. The catheters may be dilatation catheters and may be manufactured in any configuration, including rapid exchange, balloon-on-a-wire, and over-the-wire designs with single or multiple lumens. The modular construction of the catheter and releasable connection provides for rapid and easy changes in the configuration and balloon size depending on the needs of the medical procedure.

16 Claims, 5 Drawing Sheets

U.S. PATENT DOCUMENTS

| | | | |
|---|---|---|---|
| 5,300,085 | * | 4/1994 | Yock ................................. 606/191 |
| 5,334,153 | * | 8/1994 | McIntyre et al. ...................... 604/96 |
| 5,370,616 | * | 12/1994 | Keith et al. .......................... 606/194 |
| 5,397,305 | | 3/1995 | Kawula et al. ........................ 604/96 |
| 5,409,444 | | 4/1995 | Kensey et al. . | 
| 5,415,636 | * | 5/1995 | Forman ................................ 604/101 |
| 5,458,613 | | 10/1995 | Gharibadeh et al. ................. 606/194 |
| 5,498,240 | * | 3/1996 | Bagaoisan et al. .................... 604/96 |
| 5,507,731 | | 4/1996 | Hernandez et al. ................. 604/264 |

\* cited by examiner

CATHETERS HAVING A REUSABLE PROXIMAL BODY

This is a continuation of application Ser. No. 08/265,602 which was filed on Jun. 24, 1994 abandoned.

FIELD OF THE INVENTION

The present invention relates in general to the field of medical catheters and more particularly, to catheters which incorporate separable components which may be reused.

BACKGROUND OF THE INVENTION

Catheters provide for the diagnosis and treatment of disease without invasive surgery and, accordingly, are widely used for a variety of medical procedures. Unfortunately, the vast majority of catheters available today are manufactured and packaged as entirely disposable, single use devices. While these conventional catheters are undeniably beneficial in shortening hospital stays and in reducing complications associated with surgery, the precision and quality control required to fabricate these instruments makes them expensive to produce. This is particularly true for disposable catheters. Moreover, the use of disposable catheters tends to increase the amount of medical waste generated, to increase the amount of packaging waste generated and eliminate the ability to adapt the configuration of the catheter to specific operating conditions.

These and other limitations associated with the use of entirely disposable catheters are particularly well illustrated by catheters used for the treatment of vascular diseases. Over the last decade a medical procedure known as angioplasty has become widely accepted as a safe and effective method for opening stenoses throughout the vascular system and particularly for opening stenoses in the coronary arteries. The most common form of angioplasty practiced to date is known as percutaneous transluminal coronary angioplasty (PTCA).

In virtually all forms of PTCA, a dilatation catheter having an inflatable balloon at its distal end is guided into a patient's artery and maneuvered within the artery until the balloon is positioned across the narrowing stenosis responsible for inadequate blood flow to the heart. Generally, a thin guide wire is used to maneuver and direct the catheter into position. The balloon is then inflated for a brief period, usually for no more than a few minutes, in order to displace the plaque or other obstruction causing narrowing in the artery. The deflated catheter is withdrawn when the stenosis has been opened and blood is once again flowing adequately. Thus, in contrast to the serious risks and complications previously associated with open-heart surgery, PTCA can be utilized to open blocked coronary arteries using only a small vascular incision through which the dilatation catheter is inserted and operated.

Several different types of entirely disposable dilatation catheters are currently in use and may be generally classified based on their interaction with the guide wire. One common dilatation catheter design is known as the "fixed-wire" or integrated "balloon-on-awire" dilatation catheter. In general, these single-lumen catheters utilize a relatively small diameter guide wire positioned within the inflation lumen and fixed to the distal end of the dilatation balloon. This design produces a low-profile assembly which is able to cross severely narrowed lesions and to navigate tortuous vascular pathways. More recent balloon-on-a-wire designs allow the catheter to be removed while leaving the guide wire in place across the stenosis.

Another common type of dilatation catheter is known as an "over-the-wire" balloon catheter. This dual-lumen device typically utilizes a relatively large lumen for passage of a guide wire and injection of angiographic visualization dye to assist in the placement of the expansible balloon. A second parallel lumen is provided for inflation and deflation of the balloon.

More recently "rapid exchange" catheters have been developed to allow the quick removal of the catheter from the patient while leaving the guide wire in place. One such rapid exchange system, utilizes a conventional inflation lumen and a relatively short guiding or through lumen slidably received over a guide wire at the distal end of the catheter. The distal portion is permanently fused to the catheter body tube which is formed of a flexible material that allows the catheter to be pushed through curved vascular pathways.

Other "rapid exchange" catheter designs use a dedicated guide wire lumen provided with a longitudinal split seam. These designs enable the operating physician to remove the catheter by simply grasping the catheter's proximal end and pulling the catheter tube off of the guide wire. Still other designs use a blade to split the catheter upon its removal from the patient. For example a sharpened blade may be mounted within the central bore of a modified Y-connector to slit the catheter and separate it from the guide wire as it is extracted.

While these disposable catheter designs have proven effective under various conditions, the lack of reusability drives up the costs associated with their use while limiting the ability of the surgeon to adapt to changing or unexpected situations. For example, when a standard over-the-wire catheter configuration is used in an angioplasty procedure, several catheter components that do not come in contact with patient and are never subjected to physical stress are discarded. Similarly, when more than one size of expansible balloon is required in an operation the entire catheter assembly must be discarded and substituted with a catheter having the desired balloon size. The disposal of these technically advanced, precision manufactured instruments which are otherwise suitable for repeat use, reduces the efficiency of the entire procedure.

In an early effort to circumvent the disadvantages associated with the use of completely disposable catheters, it was suggested that they be resterilized and reused. However, such operations have proven to be unworkable in practice. Most of the currently available catheters are fabricated as substantially integral devices having many components joined or fused using permanent connections. As such they are not readily disassembled for the purpose of resterilization. Moreover, in order to reuse the catheter several delicate pieces of the assembly must be repeatedly subjected to harsh sterilization conditions, which may increase the possibility of material deterioration and subsequent malfunction.

This is particularly true of the thin walled, expansible dilatation balloon of the catheter. The balloon must exhibit a consistent inflation profile upon the application of several atmospheres of pressure. When subjected to repeated sterilization procedures the balloon may become distorted and fail to fold or expand properly. Further, any sterilization induced hysteresis may decalibrate the balloon sizing accuracy for future uses.

Similarly, the configuration of the catheter itself may preclude the efficient resterilization of the apparatus. Many standard catheters incorporate a closed system inflation lumen that must be entirely purged prior to sterilization to ensure the effectiveness of the procedure. Complete purging of the system is labor intensive, time consuming and expensive after use, if possible at all. Thus, the significant costs involved in resterilization may outweigh the costs of simply replacing the device.

Accordingly, it is an object of the present invention to provide catheters which incorporate resterilizable and reusable components.

It is another object of the present invention to provide dilatation catheters which allow for the rapid and uncomplicated substitution of components and for modified catheter configurations.

It is yet another object of the present invention to provide dilatation catheters which require less storage space than disposable catheters while simultaneously reducing the amount of packaging necessary to maintain their sterility prior to use.

SUMMARY OF THE INVENTION

These and other objectives are provided by the partially reusable catheters of the present invention. In a broad structural aspect, the invention is directed to catheters having a proximal body combined with a distal body. Preferably the catheters of the present invention include a disposable distal body having an expansible dilatation balloon and a reusable proximal body releasably joined through a connection. The proximal body, which may be selected from any one of a variety of configurations, is preferably constructed of rugged, resterilizable materials while the distal body is preferably fabricated using reliable, but relatively inexpensive materials, specifically designed for one-time use. In accordance with the teachings of the present invention, all types of catheters, including diagnostic catheters, guiding catheters, dilatation catheters, over-the-wire, balloon-on-a-wire, and rapid exchange catheter configurations may be fabricated having a reusable proximal body and a disposable distal body. These combinations reduce the unit costs of the apparatus, simplifies their fabrication, enhances their storage efficiency and decreases the amount of packaging and medical waste generated in conjunction with their use.

The unique modular construction of the reusable dilatation catheters of the present invention allows different catheter components to be substituted or interchanged depending on the specific needs of the operating physician. For example, the reusable proximal body may include a Y-connector, a Y-connector in conjunction with a tubular proximal body, a Y-connector with a integrated splitter or simply the tubular proximal body of a catheter. Similarly, the size, type or configuration of the disposable distal body or the expansible dilatation balloon may be altered. In addition a variety of connections may be used to join the selected proximal and distal bodies.

The reusable proximal bodies may be fabricated of resilient materials which are amenable to repeated sterilization through common techniques such as autoclaving, chemical exposure or radiation. Materials which are preferred for the reusable body of the catheter include glass, metal alloys such as stainless steel or Nitinol, ceramics or polymeric compounds. Further, the reusable catheter components may be configured to facilitate cleaning and sterilization by omitting small voids and other hard to clean recesses. In this regard the reusable proximal bodies may be further adapted to facilitate sterilization by the inclusion of purge valves or other mechanisms designed to improve access to the interior of the part.

The distal body of the catheters, preferably designed to be disposable, may be of variable lengths and configurations depending on the type of catheter assembly and the functions it must perform. For example, when the catheter is a rapid exchange design the distal body having the expansible balloon may be relatively short with dual lumen configuration for the insertion of the guide wire. Conversely, when an integrated balloon-on-a-wire catheter is to be used with a reusable Y-connector, the disposable distal body may constitute almost the entire length of the device. In either case, the disposable distal body is fabricated of reliable, yet cost effective disposable materials. Further, disposable distal bodies of the present invention may be coded using colors, bands, alphanumeric characters or other symbols to make them readily distinguishable in an operating environment.

The separable catheter bodies may be connected at any time, including up to and during their use. The connection may be made by hand or through the use of specially designed tools depending on the nature of the assembly and the connection configuration. While various types of releasable connections may be employed, they generally include at least one connecting member positioned on a first catheter body which is adapted to sealingly engage a second catheter body. The second catheter body optionally includes a second connecting member. For example, a disposable distal body may be releasably attached to a reusable proximal body using various connections including compression fittings, snap connectors, barbed connectors, luer connectors, or threaded assemblies. Moreover, each of the different connection types may be used in conjunction with each of the various catheter configurations depending on the needs of the operating physician.

Preferably the connection is a low profile design that does not substantially increase the circumference of the catheter body. Whatever type of connection is employed, releasable connecting members are preferably configured to allow fluid conducting communication between the reusable proximal body and the disposable distal body through at least one passage or lumen. This affords a reliable, fluid tight means for conducting inflation media to an expansible balloon at the distal end of a dilatation catheter if desired. Separate lumens can also be provided through connecting members for the insertion and tracking of the guide wire or for the injection of drugs or radiopaque markers.

Other objects, features and advantages of the present invention will be apparent to those skilled in the art from a consideration of the following detailed description of preferred exemplary embodiments thereof taken in conjunction with the associated Figures which will first be described briefly.

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated.

In particular it must be emphasized that the modular adaptability of the present invention provides for the association of a wide variety of distal and proximal bodies beyond those shown. Similarly, various connections may be used with each selected catheter configuration and the choice of connection employed with any given catheter assembly is in no way limited to the exemplary embodiments illustrated. For example, as will be disclosed in detail, it is within the scope of the present invention to reverse the orientation of male and female connecting members with respect to the proximal and distal ends of the catheter assembly or to provide a single connecting member on either the proximal body or distal body.

Similarly, any separable take apart, multi-component catheter is contemplated as being within the scope of the present invention. While it is preferred that the proximal bodies of the catheters of the present invention have the capacity for reuse, reuse is not essential to the present invention. Thus, the reusable components may be used once and disposed or resterilized and reused.

While the present invention is particularly useful for dilatation catheters, those skilled in the art will appreciate that separable or releasably engageable bodies may be used in conjunction with all types of catheters. For example the teachings of the present invention may be used to produce superior guiding catheters or diagnostic catheters. Accordingly, while the following discussion is primarily directed to dilatation catheters, the principles disclosed herein are applicable to a wide variety of catheters.

In this discussion common medical terms for catheter orientation will be used. Accordingly, the "distal" end of the catheter, guide wire or other element is the end farthest away from the physician who is using the device while the "proximal" end is the end closest to the operating physician.

Figure 1:
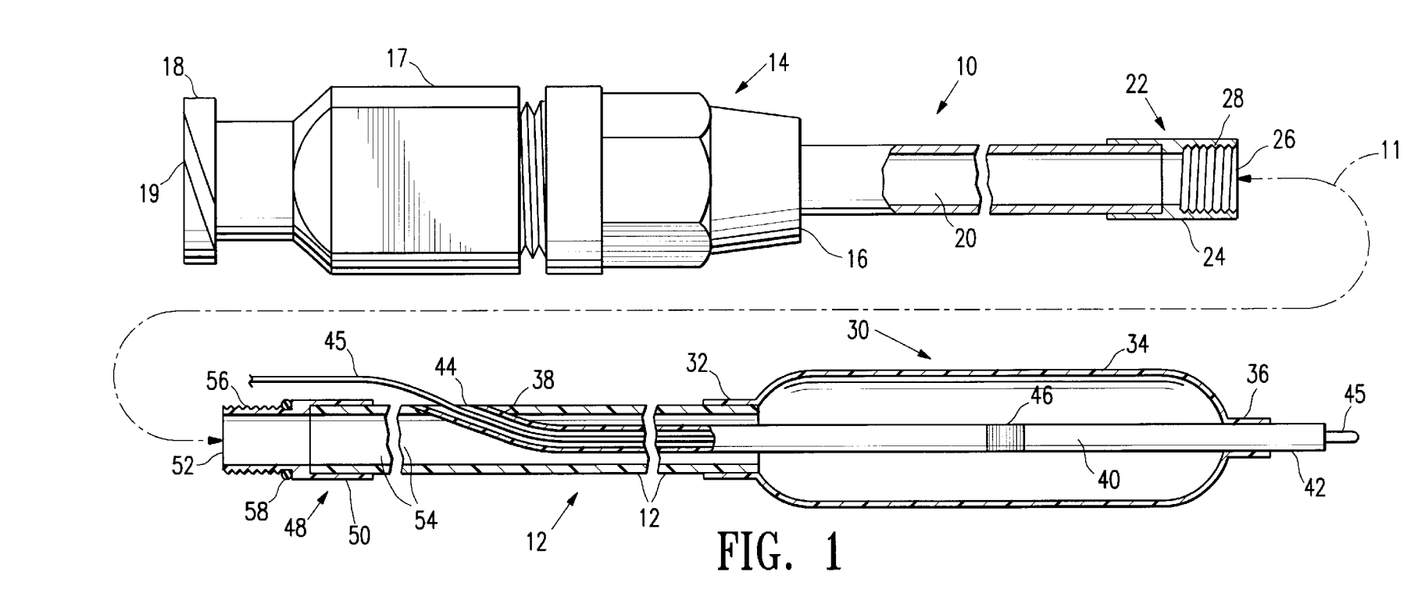
FIG. 1 is a partial fragmentary view of an exemplary disassembled rapid exchange catheter illustrating the principle of the present invention and having threaded connecting members, a reusable proximal body and disposable distal body.

Referring now to the drawing Figures, FIG. 1 shows a disassembled elongate rapid exchange balloon catheter having a reusable proximal tubular body 10 and a disposable distal tubular body 12. In the embodiment shown, the reusable proximal tubular body 10 is an elongate hypotube which is flexible, yet provides good pushability and maneuverability. That is, proximal tubular body 10 is formed of small diameter metallic tubing having a wall thickness which is comparatively thin. By way of example only, proximal tubular body 10 may be approximately 44 in. in length and have an outer diameter of 0.040 in. with an inner diameter of 0.034 in. As will be appreciated by those skilled in the art, proximal tubular body 10 may be fabricated using polymeric materials, biocompatible metals or metal alloys including stainless steel. For increased flexibility, the proximal tubular body 10 is often formed of Nitinol, a nickel-titanium alloy. Regardless of the material used, proximal tubular body 10 can be coated with Teflon® to enhance its fluid conducting properties.

As will be appreciated by those skilled in the art, the length and flexibility of the proximal tubular bodies of the present invention allows them to be coiled upon themselves for ease of storage and handling. In order to retain this self-coiled configuration, the proximal bodies of the present invention may be fitted with a luer connector adaptor (not shown) that restrains the expansion of the tubular body. More particularly, the luer connector adaptor, with catches or bores to engage proximal tubular body 10 is releasably affixed to the proximal end portion 14. Proximal tubular body 10 is then coiled and, once engaged by the catches or bores of the luer connector adaptor, will maintain that configuration for handling and storage.

At proximal end portion 14, proximal tubular body 10 is sealingly joined to fixed end fitting 16. In turn, fixed end fitting 16 is sealingly joined to luer fitting adapter 17 which includes a proximal luer connector 18 having an opening 19 at its proximal end. Preferably fixed end fitting 16 and luer fitting adapter 17 are formed of a durable material, such as metal alloys, that can withstand repeated cleaning and/or sterilization. Fixed end fitting 16 may be bonded or welded to proximal tubular body 10 using techniques known in the art. Opening 19 of proximal luer connector 18 is in fluid conducting communication with proximal bore 20 of proximal tubular body 10 thereby allowing proximal luer connector 18 to be affixed to a fluid reservoir (not shown) and used for balloon inflation purposes.

At distal end 22 of proximal tubular body 10 is sealingly attached female connecting member 24. As with fixed end fitting 16, female connecting member 24 is preferably constructed of a relatively rigid material and may be bonded or welded into place. Alternatively, female connecting member 24 may be machined directly from proximal tubular body 10. Female connecting member 24 defines screw aperture 26 which opens axially with respect to distal end 22 of proximal tubular body 10 and has female threads 28 disposed along its interior surface. When female connecting member 24 is sealingly attached to proximal body tubular 10, screw aperture 26 is in fluid conducting communication with proximal bore 20.

Distal tubular body 12 is generally made of flexible polymeric materials such as polyvinylchlorides, polyethylenes, polyolefins, fluoropolymers, polyamides, polyesters, polyimides or polypropylenes. For example, a 70/30 polyethylene tubing (employing 70% high density polyethylene and 30% low density polyethylene) is often used to provide a cost efficient, relatively flexible distal tubular body 12.

To the distal end of distal tubular body 12 is bonded, as at 32, an expansible dilatation balloon 30, having a expansible wall 34 and a distal end 36. A slit 38 is formed in the wall of distal tubular body 12 proximal to expansible dilatation balloon 30. A flexible guide tube 40 extends axially within the dilatation balloon and has a guide tube distal end 42 bonded to and sealing distal end 36 of dilatation balloon 30. Guide tube 40 may further have a radiopaque marker 46 affixed to its surface. Of course those skilled in the art will appreciate that radiopaque markers may be placed anywhere along the length of the distal body in order to facilitate tracking in the patient. In exemplary embodiments guide tube 40 may be somewhat stiffer than distal tubular body 12, being made for example of 100% high density polyethylene tubing.

Guide tube 40 extends proximally through the proximal end of dilatation balloon 30 and through the distal body tubular 12 to slit 38. Slit 38 defines a guide wire port 44 in the wall of distal body tubular 12. The proximal open end of guide tube 40 is sealed to guide wire port 44.

In other rapid exchange embodiments of the present invention, it is contemplated that the guide wire port may be positioned on the proximal body with the guide tube in communication with a proximal lumen. Here, FIG. 1 further shows guide wire 45 extending along the exterior of distal tubular body 12, through guide wire port 44, longitudinally accessing guide tube 40 and emerging at guide tube distal end 42.

At proximal end 48 of distal tubular body 12, male connecting member 50 is affixed using adhesives or other common bonding techniques. Male connecting member 50, preferably fabricated from a relatively rigid polymeric material, defines distal tube aperture 52 which opens axially at the proximal end of distal tubular body 12. Distal tube aperture 52 is in direct communication with distal lumen 54 which is defined by the walls of distal tubular body 12. Male threads 56, adapted to releasably engage female threads 28, are expressed on the exterior surface of the proximal end of male connecting member 50. Male connecting member 50 is further provided with a gasket or O-ring 58 which is placed in a position to be urged into sealing engagement upon attachment of male connecting member 50 to female connecting member 24. Gasket 58 may be made of silicone or other pliant polymeric materials and has an exemplary inner diameter of 0.028 in.

As illustrated by line 11 in FIG. 1, female connecting member 24 is adapted to sealingly receive male connecting member 50. Shown more clearly in FIG. 2, male threads 56 of male connecting member 50 are engaged with female threads 28 of female connecting member 24 to releasably connect proximal tubular body 10 end-to-end with distal tubular body 12. Both connecting members 50, 24 exhibit a low profile and do not substantially increase the absolute diameter of the catheter assembly. Upon engagement and tightening of female threads 28 with male threads 56, proximal bore 20 is sealingly connected in fluid conducting communication with distal lumen 54 through screw aperture 26 and distal tube aperture 52. Through tightening female connecting member 24, gasket 58 is urged into sealing engagement thereby preventing leakage. When proximal tubular body 10 is connected with distal tubular body 12 as shown in FIG. 2, fluid conducting communication is established longitudinally through the catheter assembly allowing inflation of expansible balloon 30 through the injection of inflation media at proximal opening 19.

Figure 2:
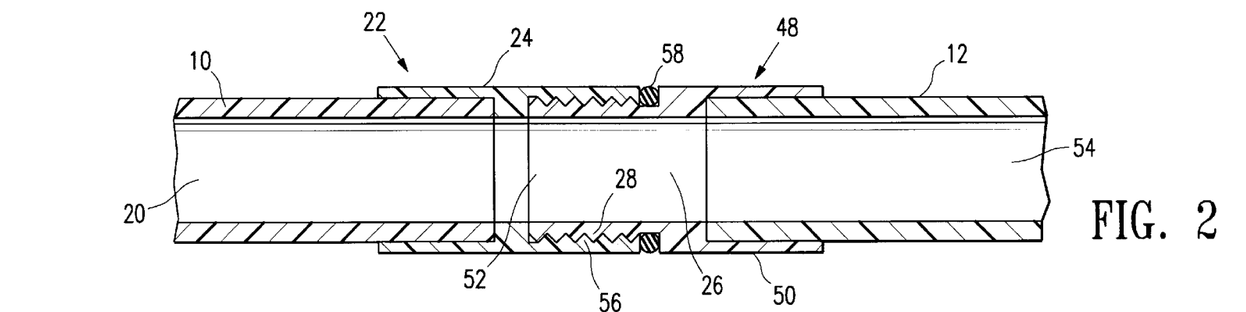
FIG. 2 is an enlarged cross-sectional view of the assembled threaded connection of FIG. 1.
Figure 3:
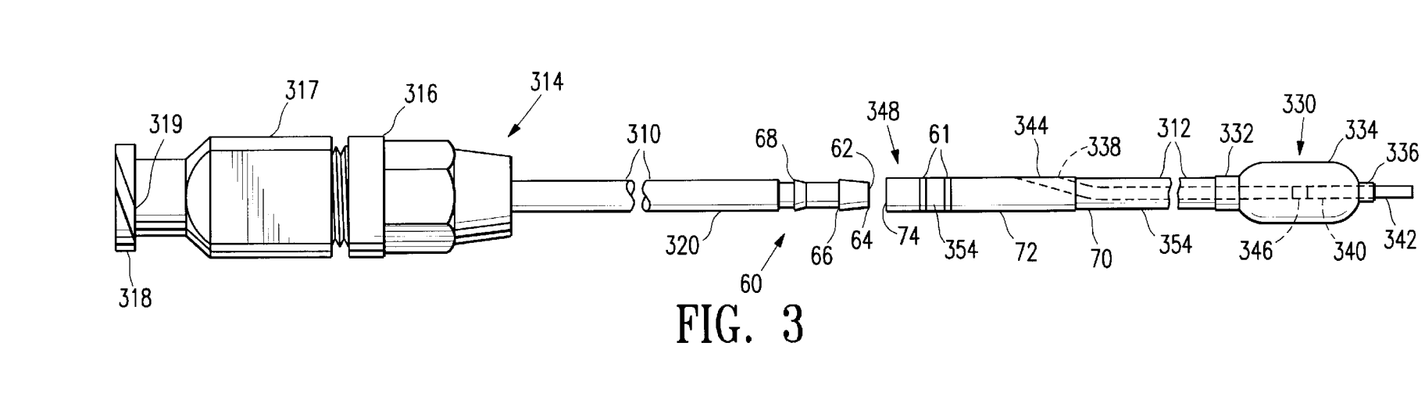
FIG. 3 is a partial fragmentary view of an alternative disassembled rapid exchange catheter having a barbed connecting member, a reusable proximal body and a disposable distal body.
Figure 4:
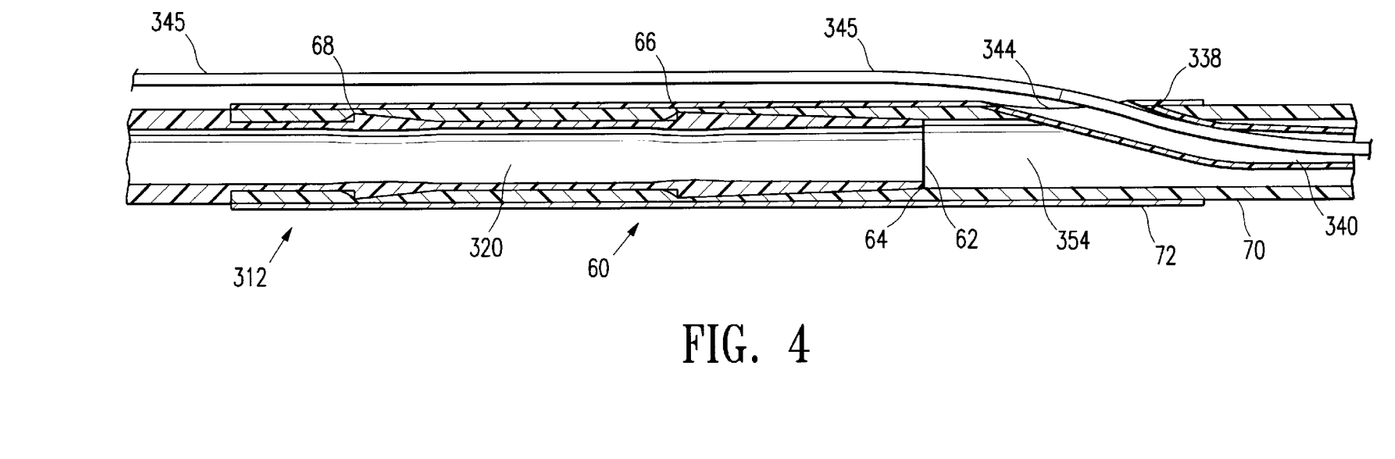
FIG. 4 is an enlarged cross-sectional view of the barbed connector assembly of FIG. 3.

An alternative embodiment of the reusable rapid exchange catheter design illustrated in FIGS. 1 and 2 is shown in FIGS. 3 and 4 with corresponding parts designated by the same reference numerals, having a prefix "3" added. For example, proximal tubular body 10 of FIG. 1 corresponds to proximal tubular body 310 of FIG. 3. In the embodiment shown in FIG. 3, both proximal end portion 314 and the balloon assembly at the distal end of the catheter are the same as the embodiment shown in FIG. 1. The primary difference between the embodiment shown in FIG. 1 and that shown in FIG. 3 is the connection used to releasably join proximal tubular body 10 with distal tubular body 12. The embodiment shown in FIG. 1 incorporates a threaded connection including male connecting member 50 and female connecting member 24 while the embodiment shown in FIG. 3 uses a barbed connecting member 60 adapted to receive distal tubular body 312. While these two embodiments are provided to illustrate the advantages of the present invention, it must be emphasized that any releasably engaging connection may be used to join the reusable proximal body and disposable distal body forming this particular catheter configuration.

FIG. 3 shows barbed connecting member 60 at the distal end of proximal tubular body 310. As with FIG. 1, proximal tubular body 310 is preferably a hypotube formed of a metallic substance such as stainless steel or Nitinol. Proximal tubular body 310 has a proximal luer connector 318 sealingly attached by fixed end fitting 316 and luer fitting adapter 317 at proximal end 314. In other embodiments of the invention, not shown in the Figures, proximal luer connector 18 or 318 may be welded or otherwise bonded directly to proximal tubular body 10 or 310. Moreover, while barbed connecting member 60 is represented as an integral extension of the walls of proximal tubular body 310 in FIGS. 3 and 4, it is contemplated that barbed connecting member 60 may be fabricated as a separate piece and affixed to proximal tubular body 310 through welding, adhesives or other techniques known in the art.

In either case, barbed connecting member 60 includes connecting end 64 defining barb aperture 62 at the distal end of proximal tubular body 310. Displaced proximally with respect to connecting end 64 is distal barb 66 and displaced proximally from distal barb 66 is proximal barb 68. An exemplary distance from the apex of distal barb 66 to the apex of proximal barb 68 is approximately 0.13 in. Both barbs are on the exterior of proximal tubular body 310 and are radially oriented with respect to proximal bore 320. Preferably proximal barb 68 has a slightly greater radius than distal barb 66. Although the illustrated embodiment incorporates two barbs those skilled in the art will appreciate that other barbed configurations may work equally well and are contemplated as being within the scope of the invention.

Also shown in FIGS. 3 and 4 is distal tubular body 312, preferably formed of a relatively flexible polymeric material such as 70/30 polyethylene tubing. As with distal tubular body 12 shown in FIG. 1, distal tubular body 312 includes a dilatation balloon 330 and a flexible guide tube 340. However, unlike the embodiment shown in FIG. 1, distal tubular body 312 does not have male connecting member 50 affixed to its proximal portion 348. Rather, distal lumen 354, defined by distal tube wall 70, terminates abruptly to form distal tube opening 74 having approximately the same internal radius as distal tubular body 312. Optional reinforcing sleeve 72 is affixed through adhesives or other conventional means to the outer surface of distal tube wall 70 along proximal portion 348 of distal tubular body 312. Although not shown in the embodiment illustrated in FIGS. 3 and 4, it must be emphasized that the present invention may be practiced without reinforcing sleeve 72. However, when used, reinforcing sleeve 72 is preferably fabricated of a material that is somewhat stiffer than the material used to form distal tube wall 70. In the embodiment shown in FIG. 3, slit 338 and corresponding guide wire port 344 are positioned so as to pass through optional reinforcing sleeve 72 as well as distal tube wall 70. The positioning of the guide wire port 344 through optional reinforcing sleeve 72 provides added strain relief helping distal tubular body 312 retain the proper configuration during use.

Distal tubular body 312 is easily attached to proximal tubular body 310 over barbed connecting member 60 which is adapted to receive distal tube opening 74. Typically, the connection is established by firmly gripping distal tubular body 312 and aligning connecting end 64 with distal tube opening 74. Distal tubular body 312 is then slid over barbed connecting member 60 to sealingly engage distal barb 66 and proximal barb 68 as shown in FIG. 4. Those skilled in the art will appreciate that the barbs 66 and 68 are configured to be slightly larger in diameter than distal tube opening 74. Accordingly, as distal tubular body 312 is slid over external barbs 66 and 68, the flexible material of distal tube wall 70 and any optional reinforcing sleeve 72 will expand slightly to accommodate them. The radial compression of distal tubular body 312 provided by the elastic memory of distal tube wall 70 and optional reinforcing sleeve 72 ensure a strong connection and tight seal.

The attachment strength provided by the use of a barbed connection according to the present invention is illustrated by the following nonlimiting example.

EXAMPLE I

Pull tests were performed to document the feasibility of using a barbed connector to releasably join a reusable proximal catheter body with a disposable distal catheter body. For testing purposes, a #20 gauge needle having an outer diameter of 0.035 in. and fabricated from stainless steel was used as a hypotube and machined to the barbed configuration shown in FIG. 3. Accordingly, for the purposes of explanation the reference numbers of FIG. 3 will be used in the description of the Example. Distal barb 66 had a diameter of approximately 0.032 in. and was 0.169 in. from connecting end 64 while proximal barb 68 had a diameter of approximately 0.035 in. and was 0.299 in. from connecting end 64 of the hypotube forming proximal tubular body 310.

Distal tubular body 312 was fabricated from 70/30 polyethylene and, unlike the embodiment shown in FIG. 3, was not reinforced. The inner diameter of distal tubular body 312 was slightly smaller than the diameters of external barbs 66, 68 measuring approximately 0.029 in. The overall length of distal tubular body 312 used in the Example was approximately 2 in. Following fabrication and sizing, distal tubular body 312 was rinsed with water and dried prior to testing.

Distal tubular body 312 was first clamped with hemostats to seal it at one end. Using grips or hemostats, barbed connecting member 60 of proximal tubular body 310 was aligned with the non-clamped end of distal tubular body 312 and force was applied to slide the tubing over distal barb 66 and proximal barb 68 thereby sealingly engaging the distal tubular body 312 and proximal tubular body 310. The force required to effect this engagement was easily provided by the technician without the use of additional tools. After the pieces were securely fastened, the assembly was placed in a standard pull test apparatus and secured.

Several assemblies, clamped in this manner, were subjected to pressure in the form of air applied through a tube in communication with proximal tubular body 310. Pressures of 0, 4, 8, 12, 16 and 20 atmospheres were applied to different clamped assemblies. Under these various pressures, which were held constant in each individual test, the connected distal tubular body 312 and proximal tubular body 310 were pulled apart at a constant rate of 20 in./min until some part of the assembly failed. The amount of stress or load on the assembly at the point of failure was monitored.

In each test, distal tubular body 312 failed or leaked before the barbed connection failed. That is, in each of the assemblies tested under different pressure, the seal provided by barbed connecting member 60 and distal tube wall 70 was not disrupted before material failure of distal tubular body 312. As expected, the amount of stress necessary to effect the rupture of distal body 312 decreased as the internal air pressure was increased, yet the connection between the proximal and distal bodies was uncompromised by the applied pressures. Those skilled in the art will appreciate that such results show that this barbed connector, or its equivalent, could easily withstand the stresses imposed by the typical inflation pressures used in dilatation catheters.

As evidenced by the data above, a strong connection may be made in accordance with the teachings of the present invention without the use of a separate reinforcing member. However, when optional reinforcing sleeve 72 is affixed to distal tubular body 312 as shown in FIGS. 3 and 4, it performs a number of different functions. For example, reinforcing sleeve 72 increases the strength of distal tubular body 312 to ensure that it will seal tightly over the barbs. Moreover, optional reinforcing sleeve 72 provides strain relief to ease the transition from semi-rigid proximal tubular body 310 to flexible distal tubular body 312. Finally, optional reinforcing sleeve 72 strengthens distal tubular body 312 in the area of the guide wire port 344, thereby reducing the chance of kinking distal tubular body 312 upon use.

FIG. 3 also shows exemplary coding bands 61 on optional reinforcing sleeve 72 along proximal portion 348 of distal tubular body 312. Coding schemes, in the form of stripes, bands, markings, characters, colors or symbols, may be used to distinguish different types, configurations or sizes of disposable distal bodies from one another. The coded distal bodies are then easily identified and selected in the operating environment by type, size, balloon configuration or any other desired criteria.

The markings or colors used to specify the desired features may be placed in any visible location on the disposable distal body. Moreover, several different features of a particular coded distal body can be specified by using a different type of coding scheme for each feature. For example, in the embodiment shown in FIG. 3, optional reinforcing sleeve 72 may be different colors to easily identify the length of dilatation balloon 330. Similarly, the diameter of distal tube opening 74 may be denoted by the number or thickness of coding bands 61 imprinted on the distal body. Of course those skilled in the art will appreciate that any distinguishing feature or features of a disposable distal body may be communicated using various coding schemes such as those described above. It will further be appreciated that any coding scheme conveying the desired information may be used in connection with any of the disposable distal bodies of the present invention and are not limited to the embodiments shown in the Figures.

Prior to the performing surgery, the catheter bodies shown in FIGS. 1–4 are removed from any packaging and prepped for use. In some instances the entire catheter may be preassembled and removed from sterile factory packaging ready for use. Alternatively, the disposable distal body will be removed from its packaging and affixed to the reusable proximal body under aseptic conditions at the site of the surgery. In such cases the disposable distal body is preferably coded to provide easy identification and allow rapid selection of the desired distal body. For example, in FIG. 1 proximal tubular body may have been autoclaved or otherwise sterilized at the hospital. In this case, distal tubular body 12 could be removed from its packaging and connected with proximal tubular body 10 in the operating area. The catheter may be assembled using tools especially adapted for the task and included in the packaging or by simply by hand.

For the rapid exchange catheter configurations shown in FIGS. 1–4, the guide wire is positioned across the stenosis. Referring to FIG. 1, the distal end of the catheter assembly, via its distal opening 42, is then inserted over the proximal end of the guide wire (outside of the patient's body) and pushed along guide wire 45, within the guide catheter (not shown), causing guide wire 45 to traverse flexible guide tube 40. The collapsed dilatation balloon continues to pass along the guide wire inside the patient until it enters the treatment area where its motion is stopped. Inflation fluid is then injected via proximal opening 19 and is conducted through proximal bore 20 and distal lumen 54 to inflate dilatation balloon 30.

If desired, the entire catheter may be rapidly withdrawn after deflation of the balloon by pulling it proximally to cause the balloon and guide tube to ride along the guide wire. Unlike prior art unitary catheter structures, the original distal tubular body is simply disengaged from the reusable proximal tubular body and discarded rather than discarding the entire catheter. A second distal tubular body, with an appropriate configuration or dilatation balloon, may then be attached to the same proximal body and reinserted into the patient using the extending proximal end of the guide wire.

Following completion of surgery, the catheter assembly is removed from the patient and taken apart using normal procedures for handling biologically contaminated instruments. For example, with respect to FIGS. 3 and 4, disposable distal tubular body 312 is detached by hand or with special tools and discarded. In direct contrast to prior art dilatation catheters, reusable proximal tubular body 310 is cleaned and resterilized thereby substantially reducing the amount of medical waste generated by the procedure. Initially, proximal tubular body 310 may be soaked in alcohol or other disinfectants to reduce the possibility of inadvertent disease transmission. After the initial soaking, proximal tubular body 310 may be purged and cleaned using fluids, preferably disinfectants, injected through proximal opening 319.

Once the reusable body of the catheter has been cleaned, it may be placed in an optional autoclave pouch or other appropriate packaging and resterilized. Those skilled in the art will appreciate that any technique commonly used to sterilize medical instruments can be used in connection with the catheters of the present invention. For example, the reusable proximal body may be sterilized using irradiation, heat, autoclaving or by exposure to liquid or gaseous disinfectants. When sterile, the reusable portion may be stored under aseptic conditions until another disposable distal body is attached and the catheter prepped for use.

Figure 5:
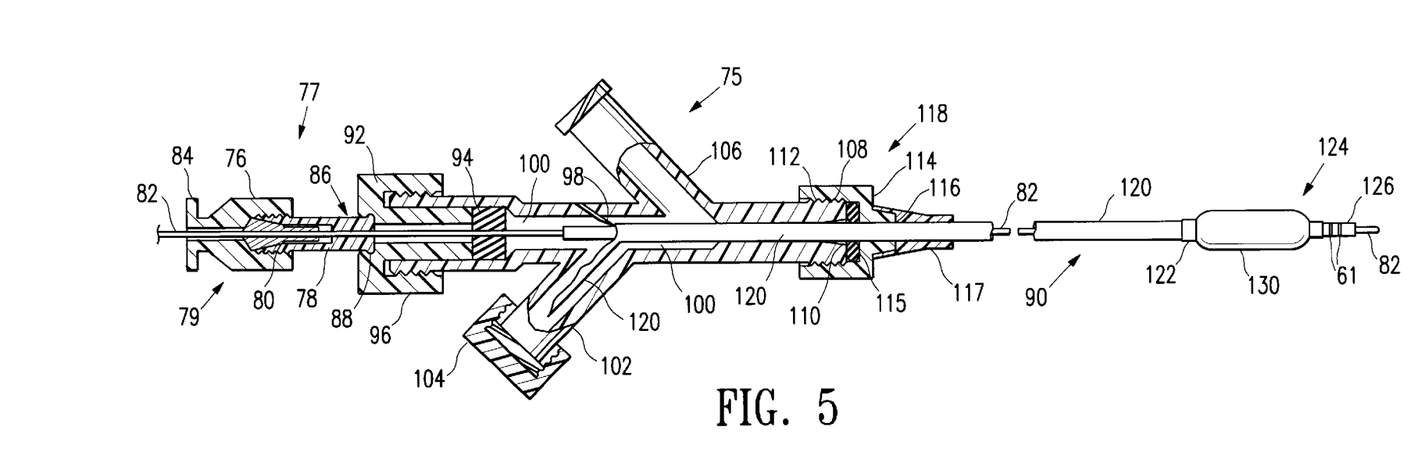
FIG. 5 is a partial fragmentary cross-sectional view of an integrated balloon-on-a-wire catheter having a reusable proximal Y-connector incorporating a catheter slitter.

Another embodiment of the present invention is shown in FIG. 5 which illustrates a balloon-on-a-wire dilatation catheter having a reusable proximal body. In this exemplary embodiment, proximal Y-connector 75 and associated fittings, such as torque assembly 77, are reusable while the entire distal body 90, attached to the Y-connector 75, is disposable. Y-connector 75 further contains a catheter slitter blade 98, mounted within the central bore 100, that can be used to split the catheter tube 120 longitudinally thereby allowing it to be pulled proximally off the guide wire 82. Disposable distal body 90, which includes dilatation balloon 130, is preferably an "integrated" or "fixed wire" arrangement having a low profile and enhanced maneuverability.

Although not essential to practice the invention, torque assembly 77 allows the rotation of the guide wire 82 upon attachment of disposable distal body 90. Releasable end-tightening arrangement 79 includes cap 76 which screws onto main body 78 and tightens down on a collet 80 around guide wire 82 running transversely through Y-connector 75. When tightened, collet 80 functions to retain the relative longitudinal position of guide wire 82. The proximal end of torque assembly 77 may be easily fitted with a proximal luer connector 84 thereby allowing Y-connector 75 to be flushed and cleaned in accordance with the teachings of the present invention.

Torque assembly 77 is attached to Y-connector 75 with a snap fitting 86 which includes a male member 88 that fits into a female member 92. Male member 88, affixed to torque assembly 77, rotates freely within female member 92 providing the physician with the ability to rotate guide wire 82 when it is clamped by collet 80 in order to steer the catheter to its desired position. Slightly distal of snap fitting 86 is proximal elastic grommet 94 which will deform and seal tightly against guide wire 82 and the inner walls of the Y-connector upon compression by cap 96. This effectively seals the proximal end of Y-connector 75 to allow a working inflation pressure to be maintained. An optional washer (not shown), may be placed between cap 96 and grommet 94 to avoid shearing.

Reusable Y-connector 75 is cylindrical along at least one axis and, according to the embodiment shown in FIG. 5, has a catheter slitter blade 98 mounted adjacent to guide wire 82 within central bore 100. Stripping port 102 is closed by sealing cap 104 which tightens onto and seals Y-connector 75. The end of catheter tube 120 may be attached to sealing cap 104 so that the pulling of sealing cap 104 also pulls catheter tube 120. Inflation port 106 is used to introduce inflation media, preferably a liquid, to Y-connector 75, through catheter tube 120 and into dilatation balloon 130 thereby increasing its diameter. Catheter slitter blade 98 preferably extends from central bore 100 on the opposite side from stripping port 102 so that, as catheter tube 120 is split, it naturally and easily enters stripping port 102.

FIG. 5 further shows that disposable distal body 90 includes catheter tube 120 having disposed therein, and extending from it, guide wire 82 along with a dilatation balloon 130. Preferably, disposable distal body 90 will be made of easily fabricated, cost effective polymeric materials such as polyethylene, polyamide, polyimide, polypropylene, polyvinylchloride, polyester such as polyethyleneterephthalate (PET) or polyolefin copolymer.

The distal end of Y-connector 75, having an access port 110 in direct communication with central bore 100, displays male connecting threads 108 disposed on its exterior surface. Access port 110, adapted to receive disposable distal body 90 may be proximally tapered to facilitate the loading of catheter tube 120 and guide wire 82 into Y-connector 75. In any case, male connecting threads 108 are engaged with female connecting threads 112 of compression hub 114 to releasably connect compression hub 114 to Y-connector 75. Compression hub 114 further defines radial bore 116 at its distal end which allows catheter tube 120 to traverse hub 114, pass through access port 110 and into central bore 100. In order to prevent catheter tube 120 from kinking, compression hub 114 preferably includes a strain relief member 117 that extends distally. Finally, grommet 115, which may be made from silicone or other pliant polymeric materials, is positioned between compression hub 114 and the distal end of Y-connector 75. Compression hub 114 and grommet 115, together with associated fixtures form connecting member 118. Of course those skilled in the art will appreciate that other Y-connectors having different features, configurations and connecting members may be substituted for the one detailed above and are clearly within the scope of the invention.

As shown in FIG. 5, catheter tube 120 and guide wire 82, held in place by connecting member 118, extend longitudinally from central bore 100 establishing fluid conducting communication between Y-connector 75 and catheter distal end 124. When compression hub 114 is tightened, grommet 115 will deform and seal tightly against catheter tube 120. Dilatation balloon 130 (shown here in its inflated state) is sealingly affixed to catheter tube 120 at balloon proximal end 122 and in direct fluid conducting communication with central bore 100. Coding bands 61 allow for the rapid identification and selection of the desired distal end 90. In the single lumen balloon-on-a-wire embodiment shown in FIG. 5, distal catheter tip 126 is reversibly sealed by guide wire 82 to provide a working inflation pressure. By pushing at its proximal end, guide wire 82 may be disengaged at distal catheter tip 126 for deflation of dilatation balloon 130. Catheter tube 120 and dilatation balloon 130 may then be easily withdrawn from the patient while leaving guide wire 82 in place.

As with other embodiments of the present invention, reusable Y-connector 75 may be attached to disposable distal body 90 prior to packaging or assembled under aseptic conditions at the operating site by the medical staff. When assembled on site, disposable distal body 90 is preferably provided in sterile packaging with dilatation balloon 130 properly folded to minimize its cross section along with a length of guide wire 82. Further, as previously discussed, disposable distal body 90 is preferably coded to rapidly provide operating personnel with selected information. In contrast, the reusable proximal body, including Y-connector 75, has preferably been used previously and resterilized on site.

To assemble this embodiment of the present invention, guide wire 82 and catheter tube 120 are threaded or "backloaded" through any strain relief member 117 and into radial bore 116 at the distal end of compression hub 114. At this point, compression hub 114 is not tightened against Y-connector 75 leaving pliant grommet 115 in an undeformed state. Guide wire 82 and catheter tube 120 pass through grommet 115, compression hub 114 and, assisted by its proximally tapered access port 110, into central bore 100. Guide wire 82 passes through Y-connector 75 and extends proximally from luer connector 84 while the proximal end of catheter tube 120 enters central bore 100, past catheter slitter blade 98 and into stripping port 102. Optional features may be incorporated in Y-connector 75 to guide catheter tube 120 and guide wire 82 into position for use. For example, a flanged ledge (not shown) could be placed in central bore 100 to guide catheter tube 120 into stripping port 102 after it has been cut by blade 98. Further, a tube in central bore 100 (not shown) may be used to assist the threading of guide wire 82 through central bore 100 and out luer port 84. Upon proper positioning of catheter tube 120 in Y-connector 75, compression hub 114 is tightened, deforming grommet 115 and securing catheter tube 120 in place. At the same time, cap 76 is tightened down on collet 80 securing guide wire 82.

Following engagement of disposable distal body 90 with Y-connector 75 using connecting member 118, dilatation balloon 130 of the intact assembly is directed to the stenotic location in the patient using torque assembly 77 and inflated through inflation port 106.

Should a different dilatation balloon be needed, disposable distal body 90 may be removed from the patient and disengaged from guide wire 82 and Y-connector 75 by splitting catheter tube 120 on slitter blade 98 as it is extracted through stripping port 102 along with deflated dilatation balloon 130. Y-connector 75 may also be easily disengaged from guide wire 82 by loosening cap 76 thereby leaving guide wire 82 in place, traversing the stenosis and allowing for the rapid replacement of the catheter assembly. Yet, unlike prior art disposable catheters, the same Y-connector and associated fixtures may be reused with a new disposable distal body 90. A second sterile disposable distal body 90, preferably coded to allow easy identification and with the guide wire removed, is simply threaded on the implanted guide wire 82, affixed to the reusable Y-connector using connecting member 118 as previously described and directed to the occlusion.

After the operation and removal from the patient, disposable distal body 90 is disengaged from reusable Y-connector 75 and discarded. Reusable Y-connector 75 may then be cleaned and resterilized according to standard laboratory procedures. As with other embodiments of the invention, reusable Y-connector 75 is preferably manufactured of strong resterilizable materials such as glass, metal alloys, or engineering plastics. In addition, specific components of Y-connector 75 may be treated to increase their resiliency under harsh sterilization conditions. For example, the brass typically used to form collet 80 may be treated with any number of anti-corrosive, anti-wear materials such as molybdenum, graphite, tungsten, and inorganic zinc. Similarly, catheter slitter blade 98, grommet 115 and proximal elastic grommet 94 may be treated with silicone to promote wear resistance. The cleaning of the reusable portion may be facilitated by the configuration of the piece or addition of features such as proximal luer connector 84 which allow the interior of Y-connector 75 to be purged. After cleaning and sterilization the part is stored under aseptic conditions until needed.

Figure 9:
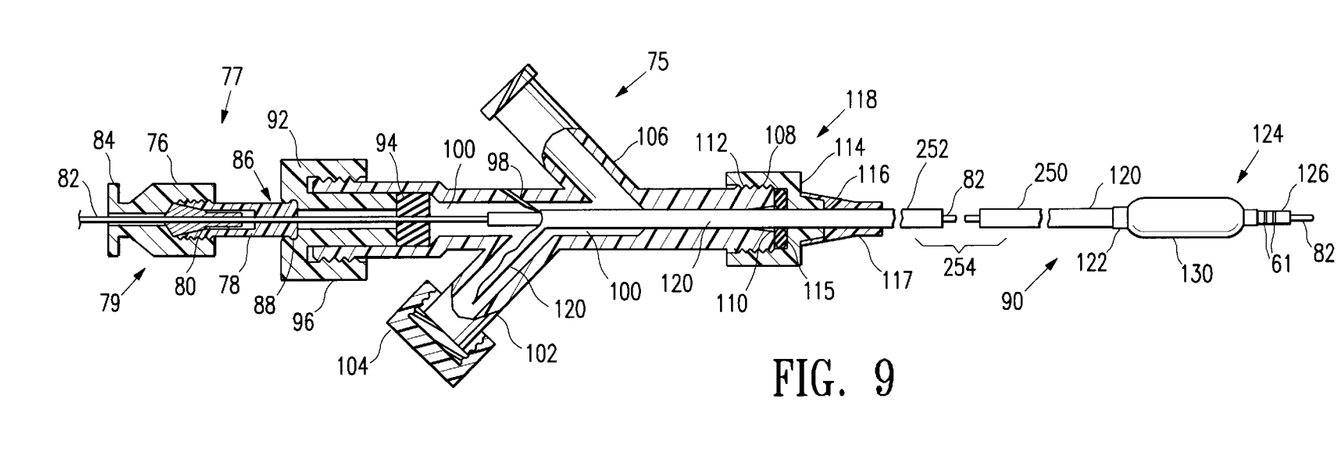
FIG. 9 is a partial fragmentary cross-section view of an integrated balloon-on-a-wire catheter having a distal shaft section releasably connected to a proximal shaft section.
Figure 10:
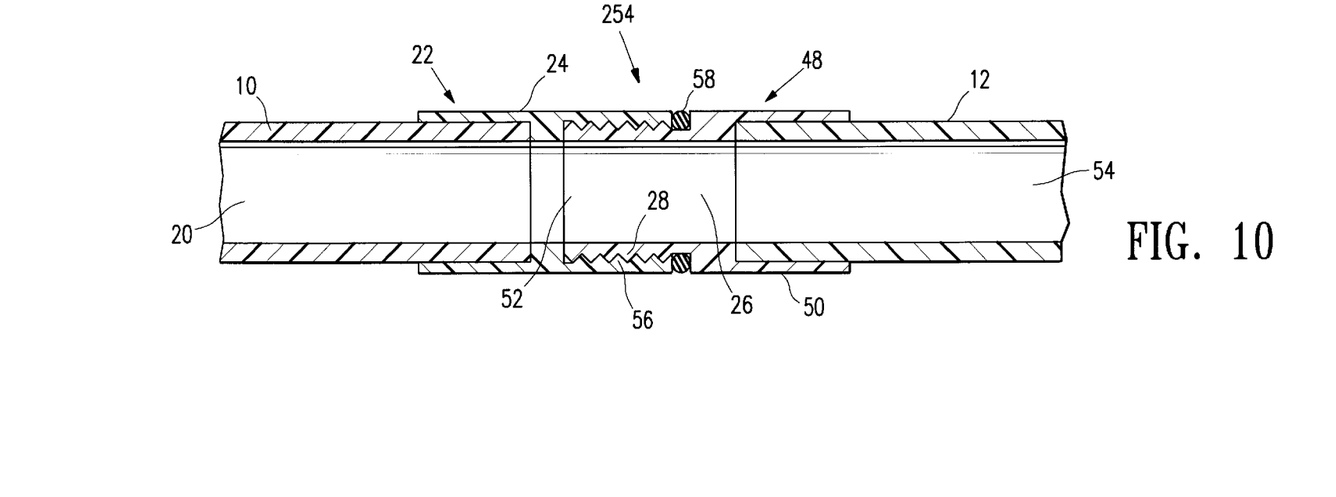
FIG. 10 is a an enlarged cross-sectional view of the integrated balloon-on-a-wire catheter of FIG. 9 illustrating an exemplary threaded connection.

In other embodiments of the present invention, a Y-connector without a slitter blade may be used as the reusable proximal end. The Y-connector may further have an optional, reusable tubular body permanently affixed to its distal end. As with the catheter assembly shown in FIG. 5, the disposable distal body may incorporate a single lumen configuration with a disengageable guide wire. FIG. 9 illustrates a catheter assembly similar to the catheter assembly shown in FIG. 5, having a single lumen configuration, with a distal shaft section 250 releasably connected to a proximal shaft section 252 at connection 254. An exemplary threaded connection shown in FIG. 9 is illustrated in more detail in FIG. 10. In such embodiments the catheter tube may be connected to the reusable Y-connector using a connecting member, including compression fittings as described above. Moreover, the proximal end of the disposable distal body may be fitted with a second connecting member adapted to releasably engage a reciprocal connecting member fitted on the distal end of the Y-connector. In addition to compression fittings, exemplary connections which may be used in these embodiments are threaded connectors including luer connectors, snap connectors and barbed connectors. Further, each different connection may be combined with all types of disposable distal bodies including those used in dilatation catheters, over-the-wire, balloon-on-a-wire and rapid exchange catheter configurations. Finally, in these and other embodiments it is clearly within the scope of the invention to reverse the orientation of male and female connecting members with respect to the proximal and distal ends of the catheter assembly. Similarly, when a single connecting member is used, it is within the scope of the invention to place it on either the proximal body or distal body.

As with the embodiments previously described, catheter configurations incorporating a Y-connector without a blade could be provided in an assembled state or sold separately. Preferably, the reusable proximal body has previously been used and resterilized at the hospital. When assembled on site, the operating staff selects the desired disposable distal body, optionally coded to provide rapid identification, including a guide wire, catheter body and dilatation balloon. Depending on the selected configuration of the distal body, the proximal end of the guide wire is threaded through the reusable Y-connector to extend from its proximal end. For example, this step may not necessary if a certain rapid exchange configurations are selected. The proximal section of the disposable distal body, with or without a connecting member, is then releasably engaged and secured with the suitably adapted connecting member at the distal end of the Y-connector. Once assembled, the catheter is then inserted in the patient and directed to the stenotic lesion.

Should a different dilatation balloon or a change in catheter configuration be desired following insertion, the disposable distal body may be removed from the patient with the dilatation balloon. Preferably, the guide wire is left in place across the occlusion. Unlike the embodiment shown in FIG. 5 the catheter tube is not pulled through the Y-connector to remove it from the patient. Rather, the Y-connector and disposable distal body are both removed proximally over the guide wire. The used disposable distal body is disengaged from the reusable proximal Y-connector and discarded. A second, sterile distal body without a guide wire is then attached to the reusable Y-connector and threaded over the previously implanted guide wire. After the operation the entire second catheter assembly is removed from the patient and disassembled. The disposable distal body is then discarded and the reusable Y-connector resterilized and stored for future use.

Figure 6:
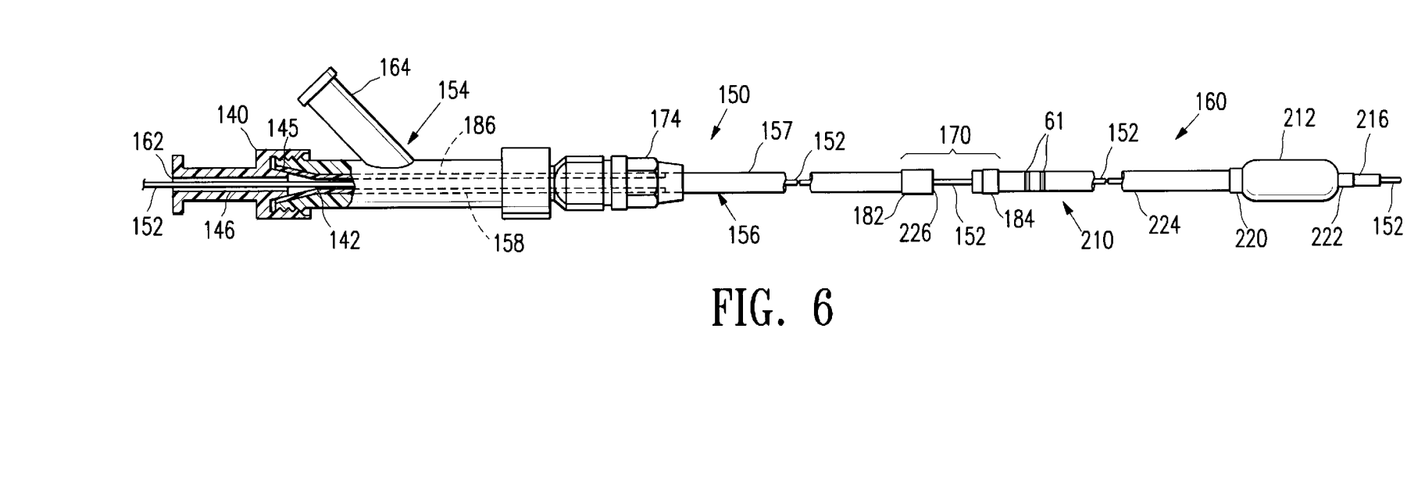
FIG. 6 is a partial fragmentary view of a dual lumen over-the-wire catheter having threaded connecting members, a disposable distal body and a reusable proximal body including a hypotube.

FIG. 6 shows a fragmentary view of a coaxial, dual lumen over-the-wire catheter having a reusable Y-connector and proximal tubular member indicated generally by reference numeral 150 adjacent to a disposable distal body 160. In accordance with the teachings of the present invention, reusable proximal body 150 may be quickly and easily attached to disposable distal body 160 to provide a catheter. An exemplary connection 170 shown in FIG. 6 is illustrated in more detail in FIG. 7. As with the other illustrated embodiments, the dual lumen catheter assembly shown in FIG. 6 may use any type of connection and is not limited to the exemplary threaded embodiment shown.

Figure 7:
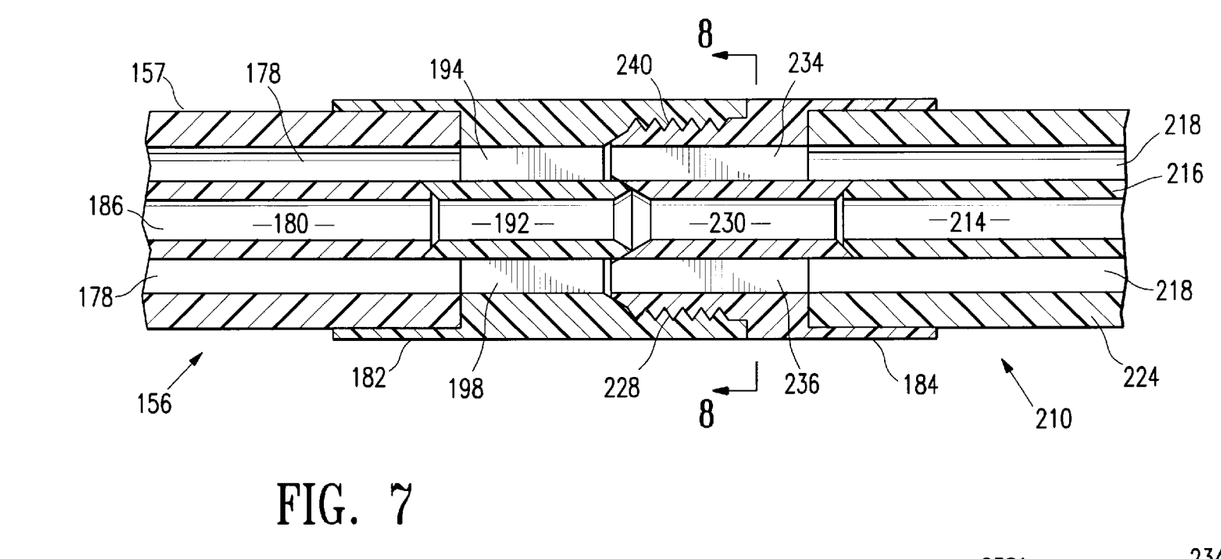
FIG. 7 is an enlarged cross-sectional view of the over-the-wire catheter of FIG. 6 illustrating its exemplary dual lumen threaded connection.

FIGS. 6 and 7 specifically show a reusable proximal Y-connector 154 sealingly connected to a coaxial tubular body 156. Coaxial tubular body 156 includes an inner lumen 180 defined by inner lumen wall 186 and a coaxially arranged peripheral annular lumen 178 defined by proximal outer wall 157. As with the embodiment of the invention shown in FIG. 5, Y-connector 154 is cylindrical along at least one axis, having an elongated central bore 158. Inflation port 164 is attached to Y-connector 154 and is in fluid conducting communication with central bore 158. The proximal end of central bore 158 terminates at aperture 142 which may flare as it extends proximally. Proximal cap 140 defines cap bore 146 extending longitudinally and defining a lumen port 162 at its proximal end. The distal end of cap bore 146 terminates in a cone 145 which seats in aperture 142 upon engagement of cap 140 with Y-connector 154.

Proximal outer wall 157 is sealingly connected to the distal end of Y-connector 154 and does not extend into central bore 158. More specifically, proximal outer wall 157 (and through it, tubular body 156) is permanently bonded to end fitting 174 using any one of a number of techniques known in the art including adhesives, welding or compression. In turn, end fitting 174 is affixed to Y-connector 154. Inner lumen wall 186, defining inner lumen 180, extends proximally from outer wall 157 through end fitting 174 before longitudinally traversing elongated central bore 158. The proximal end of inner lumen wall 186 flares radially and is seated between cone 145 and aperture 142 sealingly connecting to Y-connector 154 at its proximal end as cap 140 is engaged. Accordingly, while peripheral annular lumen 178 is in fluid conducting communication with central bore 158, inner lumen 180 remains isolated. Guide wire 152 extends proximally from inner lumen 180, traverses cap bore 146 and exits through lumen port 162.

In the embodiment shown, reusable coaxial tubular body 156 is an elongate structure of variable length preferably incorporating proximal inner lumen 180 and peripheral annular lumen 178 in a coaxial configuration. Tubular body 156 may be formed of a polymeric material similar to those previously discussed or alternatively may be formed of metallic alloys such as stainless steel or Nitinol. Both the inner and outer surfaces of tubular body 156 may be coated with a fluoropolymer (such as PTFE), silicone or other materials including low friction lubricants to provide better wetability and increased durability.

The distal end of reusable tubular body 156 is sealingly attached to threaded female connecting member 182. Female connecting member 182, part of connection 170 and shown more clearly in FIG. 7, may be made of the same materials used for tubular body 156, preferably a metallic alloy, and fused or attached using art recognized techniques. Alternatively, female connecting member 182 may be machined directly from tubular body 156. In either case, female connecting member 182 has a low profile that does not greatly increase the radial profile of the catheter assembly. As will be discussed in detail below, female connecting member 182 defines a center lumen 192 which is sealingly connected to center lumen 180 of tubular body 156. It further defines three peripheral annuli two of which are shown 194, and 198, divided by supports, which are sealingly connected to peripheral annular lumen 178. Center lumen 192 and peripheral annuli taken together define distal opening 226 of tubular body 156. Female connecting member 182 has threads 228 disposed on the tapered interior surface of distal opening 226 and adapted to receive male connecting member 184.

Shown adjacent to the distal end of reusable tubular body 156 in FIG. 6, is disposable distal body 160 which includes an elongated coaxial shaft 210 and expansible dilatation balloon 212. Coaxial shaft 210 preferably incorporates a distal inner lumen 214 defined by a distal inner lumen wall 216 and a distal peripheral annular lumen 218 defined by the outer wall 224 of shaft 210. The proximal end of dilatation balloon 220 is sealingly affixed to outer wall 224 while the distal end of dilatation balloon 222 is sealingly affixed to inner lumen wall 216. Outer wall 224 terminates within dilatation balloon 212, placing peripheral annular lumen 218 in fluid conducting communication with dilatation balloon 212. In contrast, inner lumen 214, containing guide wire 152 remains sealed off from dilatation balloon 212.

Figure 8:
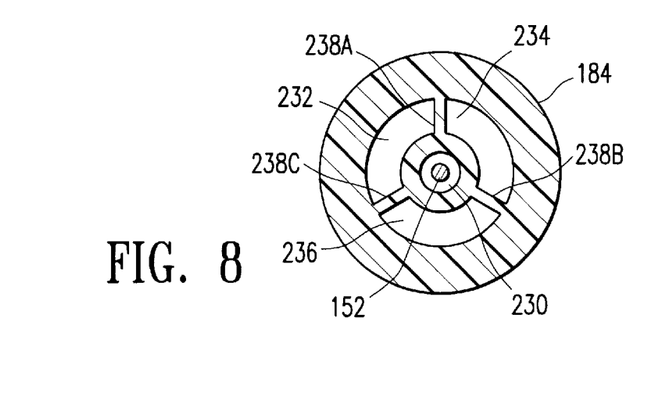
FIG. 8 is a sectional view, taken along line 8—8 of FIG. 7, showing the exemplary coaxial arrangement of the connecting member inner guide wire lumen and the peripheral fluid conducting lumen.

Sealingly affixed to the proximal end of disposable distal coaxial shaft 210 is threaded male connecting member 184. Radially, male connecting member 184 is substantially similar to female connecting member 182. FIG. 8 clearly illustrates a cross-sectional view of male connecting member 184. Male connecting member 184 defines a center lumen 230 which is sealingly connected to center lumen 214 of distal shaft 210. It further defines three distal peripheral annuli 232, 234, and 236, divided by distal supports 238A, 238B, 238C, which are sealingly connected to peripheral annular lumen 218. Center lumen 230 and distal peripheral annuli 232, 234, 236 taken together define a proximal opening of disposable distal shaft 210. Further, male connecting member 184 displays threads 240 disposed on its double tapered exterior proximal surface.

As shown in FIG. 7, male connecting member 184 is sealingly attached to female connecting member 182 by releasably engaging female connecting threads 228 and male connecting threads 240. The threads and mating ends of connecting members 182, 184 may be treated with an elastomeric coating to improve the seal. When mated, the double tapered ends of male connecting member 182 and receptive ends of female connecting member 184 define sealed coaxial lumens. A sealed center lumen 180, 192, 230 and 214 passes through connection 170 allowing guide wire 152 to extend from the proximal end of the catheter assembly to the distal end. At the same time, a longitudinal peripheral lumen, entirely separate from center lumen 180, 192, 230 and 214, is defined by proximal peripheral annular lumen 178, distal peripheral annular lumen 218 and the annuli of male connecting member 184 and female connecting member 182. This peripheral lumen establishes fluid conducting communication between Y-connector 154 and dilatation balloon 212. To effect inflation of dilatation balloon 212, liquid media is simply injected into inflation port 164.

As with other embodiments, reusable proximal body 150 and disposable distal body 160 may be supplied separately or assembled. During the procedure, the catheter assembly is inserted into the patient and threaded into position along guide wire 152 with dilatation balloon 212 in a deflated state. Inflation of dilatation balloon 212 is effected as previously described to reduce the occlusion. Following deflation of dilatation balloon 212, the apparatus is removed with or without guide wire 152 and disposable distal body 160 is disengaged from reusable proximal body 150. If desired, a second disposable distal body 160 may be attached to the same reusable proximal body 150 and the process repeated on the same patient using a different balloon size. Following completion of the procedure, the catheter apparatus is disassembled and reusable proximal body 150 is cleaned and resterilized in accordance with the teachings of the present invention. As previously discussed, reusable components may be specially treated or configured to facilitate resterilization procedure and increase their durability. After resterilization reusable proximal body 150 is stored under aseptic conditions until a disposable distal body is again attached and the assembly is prepped for use.

A catheter assembly having a substantially reusable distal body is also provided in accordance with the teachings of the present invention. This catheter assembly, a balloon-on-a-wire configuration with a single inflation/guide wire lumen similar to that shown in FIG. 5, is opened at the distal end by disengaging the guide wire. By disengaging the guide wire, the catheter may be removed while leaving the guide wire in place across the stenosis. The disengagement of the guide wire and opening of the single lumen allows easy purging of the catheter assembly using standard equipment. After cleaning, the dilatation balloon may be tested and reset or replaced. Reengaging a guide wire at the distal end of the catheter seals the lumen for inflation of the balloon. The intact catheter assembly may then be resterilized and packaged.

Those skilled in the art will further appreciate that the present invention may be embodied in other specific forms without departing from the spirit or central attributes thereof. In that the foregoing description of the present invention discloses only exemplary embodiments thereof, it is to be understood that other variations are recognized as being within the scope of the present invention. Accordingly, the present invention is not limited to the particular embodiments which have been described in detail herein. Rather, reference should be made to the appended claims to define the scope and content of the present invention.

What is claimed is:

1. An elongated intravascular catheter comprising:

a generally tubular distal catheter shaft section having a proximal end, a distal end, and a single lumen extending therein to a port in the distal end, said distal shaft section having no more than one lumen and being configured for advancement through a patient's blood vessel;

an elongated proximal catheter shaft section having a proximal end, a distal end, and a single lumen extending therein to a port in the distal end, said proximal shaft section having no more than one lumen and being releasably connected to the distal shaft section so that the lumen of the distal shaft section is in fluid communication with the lumen in the proximal shaft section; and a balloon on the distal shaft section having an interior in fluid communication with the lumen of the distal shaft section and the lumen of the proximal shaft section.

2. The catheter of claim 1 including a sealing member in the lumen of the distal shaft section configured to releasably sealingly engage a guidewire.

3. The catheter of claim 1 including a guidewire disposed within the proximal and distal shaft section lumens wherein the distal end of the distal shaft section is configured to releasably sealingly engage the guidewire disposed therein.

4. The catheter of claim 1 including a plurality of barbs.

5. The catheter of claim 1 including at least one radially extending barb disposed adjacent to said distal end of said proximal catheter shaft section and adapted to connect to said proximal end of said distal shaft section.

6. The catheter of claim 1 including a first connecting member sealingly affixed to said distal end of said proximal catheter shaft section and a second connecting member sealingly affixed to said proximal end of said distal catheter shaft section, said first connecting member adapted to releasably connect to said second connecting member.

7. The catheter of claim 6 wherein said first and said second connecting members are threaded.

8. The catheter of claim 1 wherein said proximal catheter shaft section is an elongated hypotube formed of a material selected from the group consisting of stainless steel and Nitinol.

9. The catheter of claim 1 wherein said distal catheter shaft section is provided with indicia for indicating characteristics of said distal catheter shaft section.

10. The catheter of claim 9 wherein the indicia on said distal catheter shaft section includes at least one of a stripe, a bond, a marking, a character and a symbol.

11. The catheter of claim 1 including a connecting member sealingly affixed to said distal end of said proximal catheter shaft section which is releasably connected to said proximal end of said distal catheter shaft section.

12. The catheter of claim 11 wherein said connecting member is selected from the group consisting of compression fittings, snap fittings and barbed connectors.

13. A distal catheter shaft section which is configured to be releasably engaged with a proximal catheter shaft section and to be inserted within a body lumen, said distal catheter shaft section comprising;
   an elongated, body having a proximal end, a distal end and a single lumen extending therein to a port in the distal end of the distal shaft section, said proximal end configured to releasably engage a proximal catheter shaft section; and
   a balloon on the distal shaft section having an interior in fluid communication with the lumen of the distal shaft section.

14. A method for performing medical procedures using a catheter comprising the steps of:
   providing a catheter with a generally tubular distal catheter shaft section having a proximal end, a distal end and no more than one lumen extending therein to a port in the distal end, a proximal catheter shaft section having a proximal end, a distal end and no more than one lumen extending therein, and a releasable connection sealingly connecting said distal end of said proximal catheter shaft section and said proximal end of said distal catheter shaft section in fluid communication, and a balloon on the distal shaft section having an interior in fluid communication with the lumen of the distal shaft section and the lumen of the proximal shaft section;
   inserting at least a distal portion of said proximal catheter shaft section into a patient;
   pulling the proximal end of the proximal shaft section to withdraw said distal catheter shaft section from said patient and
   disengaging said distal catheter shaft section from said proximal catheter shaft section.

15. The method of claim 14 further comprising the additional step of attaching a second distal catheter shaft section to said proximal catheter shaft section at the connection to provide a second catheter after said disengaging step.

16. The method of claim 15 further comprising the additional step of sterilizing said proximal catheter shaft section prior to attaching said second distal catheter shaft section.

* * * * *